(12) United States Patent
Buettelmann et al.

(10) Patent No.: US 7,618,973 B2
(45) Date of Patent: Nov. 17, 2009

(54) ISOXAZOLO-PYRAZINE DERIVATIVES

(75) Inventors: Bernd Buettelmann, Schopfheim (DE); Roland Jakob-Roetne, Inzlingen (DE); Henner Knust, Rheinfelden (DE); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/277,326

(22) Filed: Nov. 25, 2008

(65) Prior Publication Data
US 2009/0143407 A1 Jun. 4, 2009

(30) Foreign Application Priority Data
Dec. 4, 2007 (EP) .................................. 07122271

(51) Int. Cl.
*A61K 31/4965* (2006.01)
(52) U.S. Cl. .................. 514/255.05; 544/336; 544/353; 548/240
(58) Field of Classification Search ............ 514/255.05; 544/336, 353; 548/240
See application file for complete search history.

(56) References Cited

U.S. PATENT DOCUMENTS

| 4,639,266 A | 1/1987 | Heubach et al. |
| 2003/0055085 A1 | 3/2003 | Wagenen et al. |
| 2004/0006226 A1 | 1/2004 | Ladduwahetty et al. |

FOREIGN PATENT DOCUMENTS

| DE | 3525205 | 3/1986 |
| GB | 2336589 | 10/1999 |
| JP | 2007/230909 | 9/2007 |
| WO | WO 01/29015 | 4/2001 |
| WO | WO 01/34603 | 5/2001 |
| WO | WO 02/50062 A2 | 6/2002 |
| WO | WO 02/081474 A1 | 10/2002 |
| WO | WO 03/004027 | 1/2003 |
| WO | WO 03/015771 | 2/2003 |
| WO | WO 03/044017 | 5/2003 |
| WO | WO 2004/048349 | 6/2004 |
| WO | WO 2005/014553 | 2/2005 |
| WO | WO 2005/118568 | 12/2005 |
| WO | WO 2005/123672 A2 | 12/2005 |
| WO | WO 2006/037480 | 4/2006 |
| WO | WO 2006/044617 | 4/2006 |
| WO | WO 2006/069155 | 6/2006 |
| WO | WO 2007/009275 | 1/2007 |
| WO | WO 2007/039389 | 4/2007 |
| WO | WO 2007/052843 | 5/2007 |
| WO | WO 2007/076260 | 7/2007 |
| WO | WO 2007/092751 | 8/2007 |
| WO | WO 2008/025539 | 3/2008 |
| WO | WO 2008/025540 | 3/2008 |

OTHER PUBLICATIONS

McNamara et al., Psychobiology (1993), vol. 21, pp. 101-108.
Goodman et al., Tetrahedron (1999) vol. 55 pp. 15067-15070.
Abstract corresponding to JP 2007/230909 (Document B8).
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Seydel et al., J. Med. Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.

*Primary Examiner*—James O Wilson
*Assistant Examiner*—Douglas M Willis
(74) *Attorney, Agent, or Firm*—George W. Johnston; Patricia S. Rocha-Tramaloni; Kimberly J. Prior

(57) ABSTRACT

The invention relates to isoxazolo-pyrazine derivatives and their pharmaceutically acceptable salts having affinity and selectivity for the GABA A α5 receptor binding site, their manufacture, and pharmaceutical compositions containing them. The compounds of present invention are inverse agonists of GABA A α5. The invention also relates to methods for enhancing cognition and for treating cognitive disorders like Alzheimer's disease.

11 Claims, No Drawings

ISOXAZOLO-PYRAZINE DERIVATIVES

PRIORITY TO RELATED APPLICATION(S)

This application claims the benefit of European Patent Application No. 07122271.5, filed Dec. 4, 2007, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex is a membrane-bound heteropentameric protein polymer composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris water-maze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides isoxazolo-pyrazine derivatives and their pharmaceutically acceptable salts having affinity and selectivity for the GABA A α5 receptor binding site, their manufacture, and pharmaceutical compositions containing them. The compounds of present invention are inverse agonists of GABA A α5. The invention also provides methods for enhancing cognition and for treating cognitive disorders like Alzheimer's disease. The most preferred indication in accordance with the present invention is Alzheimer's disease.

In particular, the present invention is concerned with isoxazolo-pyrazine derivatives of formula I

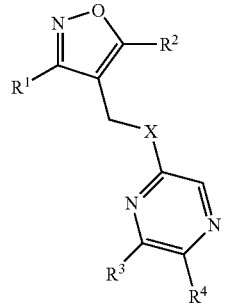

wherein $R^1$, $R^2$, $R^3$, $R^4$ and X are as described herein below.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "alkyl" denotes a saturated straight- or branched-chain hydrocarbon group containing from 1 to 7 carbon atoms, for example, methyl, ethyl, propyl, isopropyl, n-butyl, iso-butyl, sec-butyl, tert-butyl and the like. Preferred alkyl groups are groups with 1 to 4 carbon atoms.

The term "halo-$C_{1-7}$-alkyl", "$C_{1-7}$-haloalkyl" or "$C_{1-7}$-alkyl optionally substituted with halo" denotes a $C_{1-7}$-alkyl group as defined above wherein at least one of the hydrogen atoms of the alkyl group is replaced by a halogen atom, preferably fluoro or chloro, most preferably fluoro. Examples of halo-$C_{1-7}$-alkyl include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro, as well as those groups specifically illustrated by the examples herein below. Among the preferred halo-$C_{1-7}$-alkyl groups are difluoro- or trifluoro-methyl or -ethyl.

The term "hydroxy-$C_{1-7}$-alkyl", "$C_{1-7}$-hydroxyalkyl" or "$C_{1-7}$-alkyl optionally substituted with hydroxy" denotes a $C_{1-7}$-alkyl group as defined above wherein at least one of the hydrogen atoms of the alkyl group is replaced by a hydroxy group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more hydroxy group(s), in particular with one, two or three hydroxy groups, preferably with one hydroxy group, as well as those groups specifically illustrated by the examples herein below.

The term "cyano-$C_{1-7}$-alkyl", "$C_{1-7}$-cyanoalkyl" or "$C_{1-7}$-alkyl optionally substituted with cyano" denotes a $C_{1-7}$-alkyl group as defined above wherein at least one of the hydrogen atoms of the alkyl group is replaced by a cyano group. Examples of hydroxy-$C_{1-7}$-alkyl include but are not limited to methyl, ethyl, propyl, isopropyl, isobutyl, sec-butyl, tert-butyl, pentyl or n-hexyl substituted by one or more cyano group(s), preferably by one, two or three, and more preferably by one cyano group, as well as those groups specifically illustrated by the examples herein below.

The term "alkoxy" denotes a group —O—R wherein R is alkyl as defined above.

The term "aryl" denotes a monovalent aromatic carbocyclic ring system, preferably phenyl or naphthyl, and more preferably phenyl. Aryl is optionally substituted as described herein.

The term "aromatic" means aromatic according to Hückel's rule. A cyclic molecule follows Hückel's rule when the number of its π-electrons equals 4n+2 where n is zero or any positive integer.

The term "halo" or "halogen" denotes chloro, iodo, fluoro and bromo.

The term "$C_{1-7}$-haloalkoxy" or "halo-$C_{1-7}$-alkoxy" denotes a $C_{1-7}$-alkoxy group as defined above wherein at least one of the hydrogen atoms of the alkoxy group is replaced by a halogen atom, preferably fluoro or chloro, most preferably fluoro. Examples of halo-$C_{1-7}$-alkoxy include but are not limited to methyl, ethyl, propyl, isopropyl, isobutyl, sec-butyl, tert-butyl, pentyl or n-hexyl substituted by one or more Cl, F, Br or I atom(s), in particular one, two or three fluoro or chloro atoms, as well as those groups specifically illustrated by the examples herein below. Among the preferred halo-$C_{1-7}$-alkoxy groups are difluoro- or trifluoro-methoxy or -ethoxy substituted as described above, preferably —$OCF_3$.

The term "cycloalkyl" refers to a monovalent saturated cyclic hydrocarbon radical of 3 to 7 ring carbon atoms, preferably 3 to 6 carbon atoms, such as cyclopropyl, cyclobutyl, cyclopentyl, or cyclohexyl.

The term "heterocycloalkyl" refers to a monovalent 3 to 7 membered saturated monocyclic ring containing one, two or three ring heteroatoms selected from N, O and S. One or two ring heteroatoms are preferred. Preferred are 4 to 6 membered heterocycloalkyl or 5 to 6 membered heterocycloalkyl, each containing one or two ring heteroatoms selected from N, O and S. Examples for heterocycloalkyl moieties are tetrahydrofuranyl, tetrahydropyranyl, pyrrolidinyl, morpholinyl, thiomorpholinyl, piperidinyl, or piperazinyl. A preferred heterocycloalkyl is tetrahydropyranyl. Heterocycloalkyl is a subgroup of "heterocyclyl" as described below. Heterocycloalkyl is optionally substituted as described herein.

The term "heteroaryl" refers to a monovalent aromatic 5- or 6-membered monocyclic ring containing one, two, or three ring heteroatoms selected from N, O, and S, the remaining ring atoms being C. Preferably, the 5- or 6-membered heteroaryl ring contains one or two ring heteroatoms. 6-membered heteroaryl are preferred. Examples for heteroaryl moieties include but are not limited to thiophenyl, furanyl, pyridinyl, pyrimidinyl, pyrazinyl, pyrazolyl, imidazolyl, oxazolyl, isoxazolyl, thiazolyl, isothiazolyl, triazolyl, 1,2,4-oxadiazolyl, or 1,3,4-oxadiazolyl.

The term "heterocyclyl" or "heterocyclyl moiety" refers to a monovalent saturated or partially saturated 3- to 7-membered monocyclic or 9- to 10-membered bicyclic ring system wherein one, two, three or four ring carbon atoms have been replaced by N, O or S, and with the attachment point on the saturated or partially unsaturated ring of said ring system. Such bicyclic heterocyclyl moieties hence include aromatic rings annelated to saturated rings. Where applicable, "heterocyclyl moiety" further includes cases where two residues R' and R" together with the nitrogen to which they are bound form such a heterocyclyl moiety. Examples for heterocyclyl include but are not limited to tetrahydrofuranyl, tetrahydropyranyl, pyrrolidinyl, morpholinyl, thiomorpholinyl, piperidinyl, piperaziny, or hexahydrothiopyranyl, as well as their corresponding partially unsaturated derivatives.

The term "oxo" when referring to substituents on heterocycloalkyl, heterocyclyl or on a heterocycle means that an oxygen atom is attached to the ring. Thereby, the "oxo" can either replace two hydrogen atoms on a carbon atom, or it can simply be attached to sulfur, so that the sulfur exists in oxidized form, i.e. bearing one or two oxygens.

When indicating the number of substituents, the term "one or more" means from one substituent to the highest possible number of substitution, i.e. replacement of one hydrogen up to replacement of all hydrogens by substituents. Thereby, one, two or three substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

In general, the nomenclature used in this Application is based on AUTONOM™ v.4.0, a Beilstein Institute computerized system for the generation of IUPAC systematic nomenclature.

For explanation, the following nomenclature has been used:

The residue of formula a

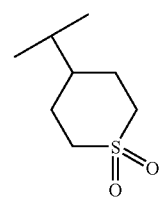

(a)

is named 1,1-dioxo-tetrahydro-thiopyran-4-yl or tetrahydrothiopyran-4-yl-1,1-dioxode, whereas a residue of formula b

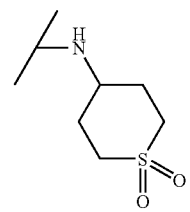

(b)

is named 1,1-dioxo-hexahydro-1lambda6-thiopyran-4-yl.

The residue of formula c (c)

is named 1,1-dioxo-thiomorpholin-4-yl or thiomorpholin-4-yl-1,1-dioxide, whereas the residue of formula d (d)

is named 1,1-dioxo-1lambda-6-thiomorpholin-4-yl-methanone.

In detail, the present invention relates to compounds of the general formula (I)

I wherein
X is O or NH;
$R^1$ is phenyl, optionally substituted with one, two or three halo,
$R^2$ is H, $C_{1-4}$ alkyl or $C_{1-4}$ haloalkyl;
$R^3$ and $R^4$ each are independently
  H,
  $C_{1-7}$ alkyl, optionally substituted with one or more halo, cyano, or hydroxy,
  $C_{1-7}$ alkoxy, optionally substituted with one or more halo,
  CN,
  halo,
  $NO_2$,
  —C(O)—$R^a$, wherein $R^a$ is hydroxy, $C_{1-7}$ alkoxy, $C_{1-7}$ alkyl, phenoxy or phenyl,
  —C(O)—$NR^bR^c$, wherein $R^b$ and $R^c$ are each independently
    H,
    $C_{1-7}$ alkyl, optionally substituted with one or more halo, hydroxy, or cyano,
    —$(CH_2)_z$—$C_{3-7}$ cycloalkyl, optionally substituted by one or more B,
    and z is 0, 1, 2, 3 or 4,
    —$(CH_2)_y$-heterocyclyl, wherein y is 0, 1, 2, 3 or 4, and wherein heterocyclyl is optionally substituted by one or more A
  $R^b$ and $R^c$ together with the nitrogen to which they are bound form a heterocyclyl moiety, optionally substituted with one or more A, or
or $R^3$ and $R^4$ together form an anellated benzo ring, the benzo ring is optionally substituted by one or more E,
A is hydroxy, oxo, $C_{1-7}$ alkyl, $C_{1-7}$ alkoxy, $C_{1-7}$ haloalkyl, $C_{1-7}$ hydroxyalkyl, halo, or CN,
B is halo, hydroxy, CN, $C_{1-4}$ alkyl, or $C_{1-4}$ haloalkyl,
E is halo, CN, $NO_2$, hydroxy, $C_{1-7}$ alkyl, $C_{1-7}$ alkoxy, $C_{1-7}$ haloalkyl, $C_{1-7}$ hydroxyalkyl, $C_{1-7}$ cyanoalkyl, $C_{1-7}$ haloalkoxy, or $C_{3-7}$ cycloalkyl, or a pharmaceutically acceptable salt thereof.

In certain embodiments of the compound of formula I, X is O or NH. Each of these alternatives can be combined with any other embodiment as disclosed herein.

Further, it is to be understood that every embodiment relating to a specific residue $R^1$ to $R^4$ as disclosed herein can be combined with any other embodiment relating to another residue $R^1$ to $R^4$ as disclosed herein.

In certain embodiments of the compound of formula I, $R^1$ is phenyl, optionally substituted with one, two or three halo. Preferred halo substituents are chloro and fluoro. In case phenyl is substituted, preferably one or two optional halo substituents selected from chloro and fluoro are chosen.

In certain embodiments of the invention, $R^2$ is H, $C_{1-4}$ alkyl or $C_{1-4}$ haloalkyl. Preferably, $R^2$ is H, methyl or trifluoromethyl. In certain embodiments of the compound of formula I, $R^2$ is H or methyl, and in certain embodiments, $R^2$ is methyl.

In certain embodiments of the compound of formula I, $R^3$ and $R^4$ are as defined above.

In certain embodiments of the compound of formula I, $R^3$ is H or $R^3$ and $R^4$ together form an anellated benzo ring, i.e. a benzo ring anellated to the pyrazin moiety, whereby benzo is optionally substituted as defined herein.

In certain embodiments of the compound of formula I, $R^4$ is as described above.

In certain embodiments of the compound of formula I, $R^4$ is
  H,
  —C(O)—$R^a$, wherein $R^a$ is hydroxy, $C_{1-7}$ alkoxy, $C_{1-7}$ alkyl, phenoxy or phenyl,
  —C(O)—$NR^bR^c$, wherein $R^b$ and $R^c$ are each independently
    H,
    $C_{1-7}$ alkyl, optionally substituted with one or more halo, hydroxy, or cyano,
    —$(CH_2)_z$—$C_{3-7}$ cycloalkyl, optionally substituted by one or more B,
    and z is 0, 1, 2, 3 or 4, preferably 0 or 1,
    —$(CH_2)_y$-heterocyclyl, wherein y is 0, 1, 2, 3 or 4, preferably 0, and wherein heterocyclyl is optionally substituted by one or more A
or $R^3$ and $R^4$ together form an anellated benzo ring, the benzo ring is optionally substituted by one or more E, A is hydroxy, oxo, $C_{1-7}$ alkyl, $C_{1-7}$ alkoxy, $C_{1-7}$ haloalkyl, $C_{1-7}$ hydroxyalkyl, halo, or CN, B is halo, hydroxy, CN, $C_{1-4}$ alkyl, or $C_{1-4}$ haloalkyl, E is halo, CN, $NO_2$, hydroxy, $C_{1-7}$ alkyl, $C_{1-7}$ alkoxy, $C_{1-7}$ haloalkyl, $C_{1-7}$ hydroxyalkyl, $C_{1-7}$ cyanoalkyl, $C_{1-7}$ haloalkoxy, or $C_{3-7}$ cycloalkyl.

In certain embodiments of the compound of formula I, $R^4$ is

H,

—C(O)—$R^a$, wherein $R^a$ is hydroxy, or $C_{1-7}$ alkoxy,

—C(O)—$NR^bR^c$, wherein $R^b$ and $R^c$ are each independently

H, $C_{1-7}$ alkyl, optionally substituted with one or more halo, hydroxy, or cyano, —$(CH_2)_z$—$C_{3-7}$ cycloalkyl, optionally substituted by one or more B, and z is 0, 1, 2, 3 or 4, preferably 0 or 1, —$(CH_2)_y$-heterocyclyl, wherein y is 0, 1, 2, 3 or 4, preferably 0, and wherein heterocyclyl is tetrahydropyranyl optionally substituted by one or more A or $R^3$ and $R^4$ together form an annelated benzo ring, the benzo ring is optionally substituted by one or more E, A is hydroxy, oxo, $C_{1-7}$ alkyl, $C_{1-7}$ alkoxy, $C_{1-7}$ haloalkyl, $C_{1-7}$ hydroxyalkyl, halo, or CN, B is halo, hydroxy, CN, $C_{1-4}$ alkyl, or $C_{1-4}$ haloalkyl, E is halo, CN, $NO_2$, hydroxy, $C_{1-7}$ alkyl, $C_{1-7}$ alkoxy, $C_{1-7}$ haloalkyl, $C_{1-7}$ hydroxyalkyl, $C_{1-7}$ cyanoalkyl, $C_{1-7}$ haloalkoxy, or $C_{3-7}$ cycloalkyl.

A certain embodiment of the invention comprises the compound of formula I

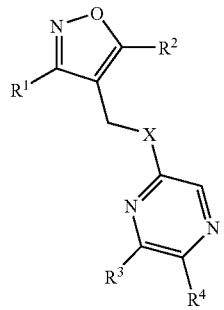

I wherein

X is O or NH;

$R^1$ is phenyl, optionally substituted with one, two or three halo, $R^2$ is H, $C_{1-4}$ alkyl or $C_{1-4}$ haloalkyl; preferably H, methyl or trifluoromethyl;

$R^3$ is H;

$R^4$ is H,

—C(O)—$R^a$, wherein $R^a$ is hydroxy, $C_{1-7}$ alkoxy, $C_{1-7}$ alkyl, phenoxy or phenyl, —C(O)—$NR^bR^c$, wherein $R^b$ and $R^c$ are each independently

H, $C_{1-7}$ alkyl, optionally substituted with one or more halo, hydroxy, or cyano, —$(CH_2)_z$—$C_{3-7}$ cycloalkyl, optionally substituted by one or more B, and z is 0, 1, 2, 3 or 4, preferably 0 or 1, —$(CH_2)_y$-heterocyclyl, wherein y is 0, 1, 2, 3 or 4, preferably 0, and wherein heterocyclyl is optionally substituted by one or more A or $R^3$ and $R^4$ together form an annelated benzo ring, the benzo ring is optionally substituted by one or more E, A is hydroxy, oxo, $C_{1-7}$ alkyl, $C_{1-7}$ alkoxy, $C_{1-7}$ haloalkyl, $C_{1-7}$ hydroxyalkyl, halo, or CN, B is halo, hydroxy, CN, $C_{1-4}$ alkyl, or $C_{1-4}$ haloalkyl, E is halo, CN, $NO_2$, hydroxy, $C_{1-7}$ alkyl, $C_{1-7}$ alkoxy, $C_{1-7}$ haloalkyl, $C_{1-7}$ hydroxyalkyl, $C_{1-7}$ cyanoalkyl, $C_{1-7}$ haloalkoxy, or $C_{3-7}$ cycloalkyl, or a pharmaceutically acceptable salt thereof.

Preferred compounds of formula I of present invention are 5-(5-methyl-3-phenyl-isoxazol-4-ylmethoxy)-pyrazine-2-carboxylic acid methyl ester, 5-(5-methyl-3-phenyl-isoxazol-4-ylmethoxy)-pyrazine-2-carboxylic acid cyclopropylmethyl-amide, 5-(5-methyl-3-phenyl-isoxazol-4-ylmethoxy)-pyrazine-2-carboxylic acid isopropylamide, 5-(5-methyl-3-phenyl-isoxazol-4-ylmethoxy)-pyrazine-2-carboxylic acid tert-butylamide, 5-(5-methyl-3-phenyl-isoxazol-4-ylmethoxy)-pyrazine-2-carboxylic acid cyclopropylamide, 5-(5-methyl-3-phenyl-isoxazol-4-ylmethoxy)-pyrazine-2-carboxylic acid (tetrahydro-pyran-4-yl)-amide, 5-(5-methyl-3-phenyl-isoxazol-4-ylmethoxy)-pyrazine-2-carboxylic acid (4,4-difluoro-cyclohexyl)-amide, 2-(5-methyl-3-phenyl-isoxazol-4-ylmethoxy)-quinoxaline, 5-[(5-methyl-3-phenyl-isoxazol-4-ylmethyl)-amino]-pyrazine-2-carboxylic acid isopropylamide, 5-[(5-methyl-3-phenyl-isoxazol-4-ylmethyl)-amino]-pyrazine-2-carboxylic acid cyclopropylamide, and 5-[(5-methyl-3-phenyl-isoxazol-4-ylmethyl)-amino]-pyrazine-2-carboxylic acid (tetrahydro-pyran-4-yl)-amide.

The present compounds of formula I (X=O) and their pharmaceutically acceptable salts can be prepared by a process comprising:

a) reacting a compound of formula II:

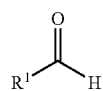

II with hydroxylamine hydrochloride in a suitable solvent, such as ethanol and water in the presence of a base, such as aqueous sodium hydroxide, to give a compound of formula III:

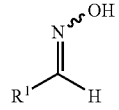

III b) reacting the compound of formula III with a chlorinating agent, such as N-chlorosuccinimide, in a suitable solvent, such as DMF, to give a compound of formula IV:

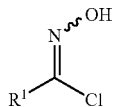

IV c1) and then either reacting the compound of formula IV with a compound of formula V:

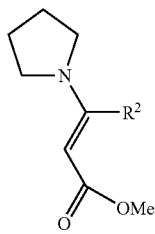

V in the presence of a suitable base, such as triethylamine, in a suitable solvent, such as chloroform, or alternatively c2) reacting the compound of formula IV with a compound of formula VI:

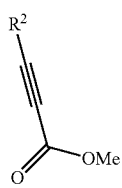

VI in the presence of a suitable base, such as triethylamine, in a suitable solvent, such as diethylether, to give a compound of formula VII:

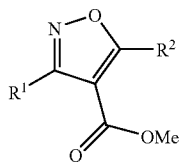

VII d) reacting a compound of formula VII with a reducing agent, such as lithiumaluminiumhydride, in a suitable solvent, such as THF, to give a compound of formula VIII:

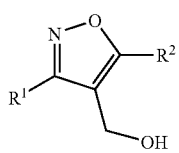

VIII i) with a compound of formula IX:

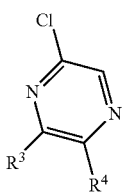

IX in the presence of a suitable base, such as sodium hydride, in a suitable solvent, such as THF, to give a compound of formula I:

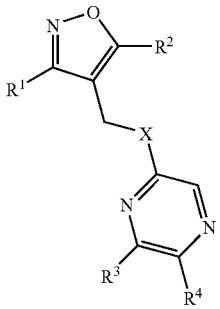

I

The present compounds of formula I (X=NH) and their pharmaceutically acceptable salts can be prepared by a process comprising:

j) reacting a compound of formula VIII:

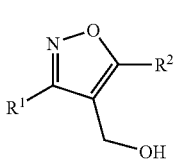

VIII with phthalimide in the presence of triphenylphosphine and diethylazodicarboxylate, in a suitable solvent, such as THF to give a compound of formula X:

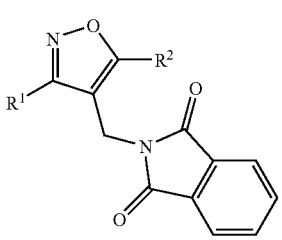

X g) reacting the compound of formula X with hydrazine, to give a compound of formula XI:

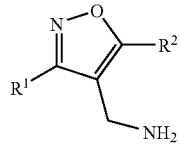

with a compound of formula IX:

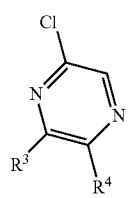

in the presence of a suitable base, such as sodium hydride, in a suitable solvent, such as THF to give a compound of formula I:

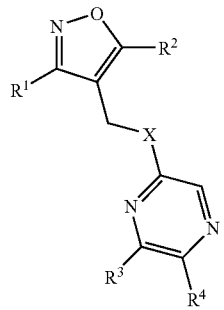

The following scheme describes the processes for preparation of compounds of formula I (X=O and NH) in more detail.

In accordance with Scheme 1, compounds of formula I can be prepared following standards methods.

Scheme 1

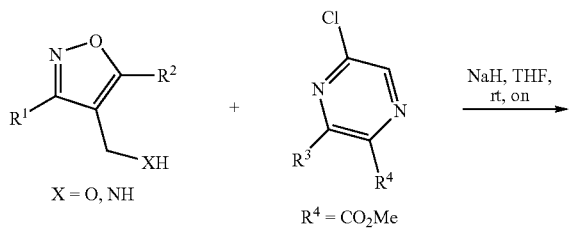

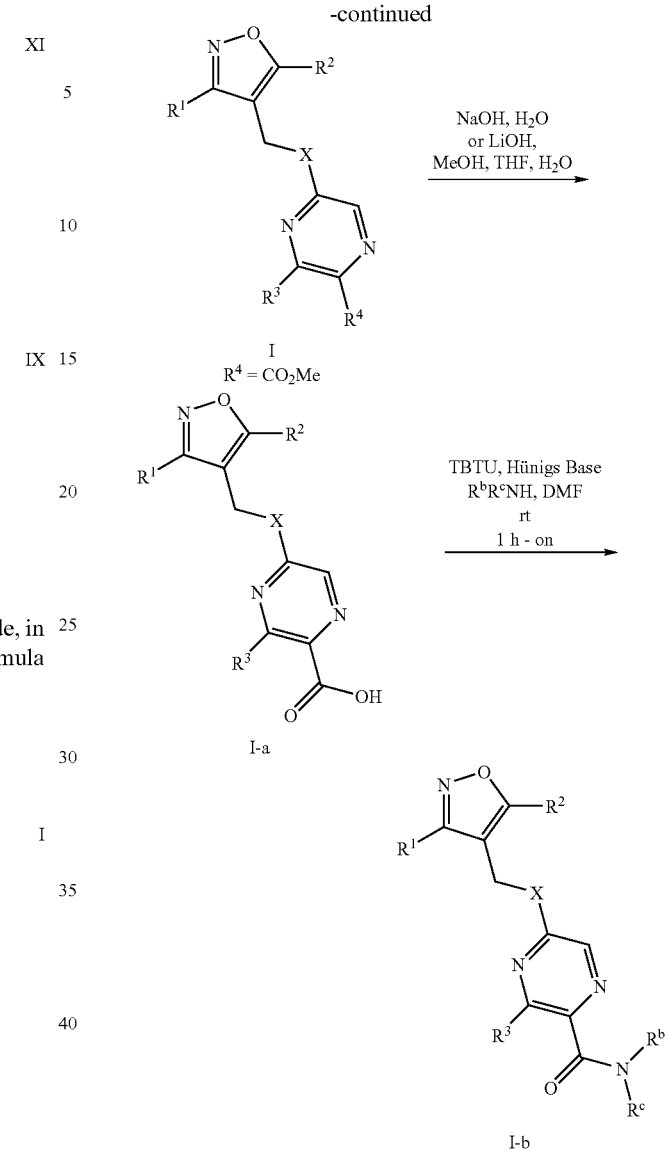

on = overnight
rt = room temperature
DMF = N,N-dimethylformamide
TBTU = O-(Benzotriazol-1-yl)-N,N,N′,N′-tetramethyluronium tetrafluoroborate As mentioned earlier, the compounds of formula I and their pharmaceutically usable salts possess valuable pharmacological properties. The compounds of the present invention are ligands for GABA A receptors containing the α5 subunit and are therefore useful in the therapy where cognition enhancement is required.

The compounds were investigated in accordance with the test given hereinafter:

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 μL (96-well plates) which contained 100 μL of cell membranes, [3H]flumazenil at a concentration of 1 nM for $\alpha 1$, $\alpha 2$, $\alpha 3$ subunits and 0.5 nM for $\alpha 5$ subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from $\alpha 5$ subunits of the rat GABA A receptor of 100 nM or less. Most preferred are compounds with a Ki (nM)<35. In a preferred embodiment the compounds of the invention are binding selective for the $\alpha 5$ subunit relative to the $\alpha 1$, $\alpha 2$ and $\alpha 3$ subunit.

Representative test results are shown in the table below:

TABLE 1

| Example | hKi (nM) |
|---------|----------|
| 1 | 29 |
| 2 | 3.1 |
| 3 | 1.2 |
| 4 | 10.8 |
| 5 | 1.9 |
| 6 | 1.2 |
| 7 | 10.6 |
| 8 | 7.4 |
| 9 | 9.6 |
| 10 | 10.4 |
| 11 | 12.1 |

"h" in "hKi" means "human".

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions, or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injectable solutions.

The dosage at which compounds of the invention can be administered can vary within wide limits and will, of course, be fitted to the individual requirements in each particular case. In general, in the case of oral administration a daily dosage of about 0.1 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition can be manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition can be manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch can be firstly mixed in a mixer and then in a comminuting machine. The mixture can be returned to the mixer, the talc can be added thereto and mixed thoroughly. The mixture can be filled by machine into hard gelatine capsules.

EXAMPLE C

Suppositories of the following composition can be manufactured:

|                  | mg/supp. |
|------------------|----------|
| Active substance | 15       |
| Suppository mass | 1285     |
| Total            | 1300     |

The suppository mass can be melted in a glass or steel vessel, mixed thoroughly and cooled to 45° C. Thereupon, the finely powdered active substance can be added thereto and stirred until it has dispersed completely. The mixture can be poured into suppository moulds of suitable size and left to cool. The suppositories then can be removed from the moulds and packed individually in wax paper or metal foil.

The following examples 1-11 are provided for illustration of the invention. They should not be considered as limiting the scope of the invention, but merely as being representative thereof.

EXAMPLE 1

5-(5-Methyl-3-phenyl-isoxazol-4-ylmethoxy)-pyrazine-2-carboxylic acid methyl ester To a solution of (5-methyl-3-phenyl-isoxazol-4-yl)-methanol (1.24 g, 6.55 mmol) in THF (12 mL) was added sodium hydride (55% dispersion in mineral oil, 0.31 g, 7.2 mmol) at 0° C. The reaction mixture was stirred for 30 min while it was allowed to warm up to room temperature. Methyl 5-chloro-pyrazine-2-carboxylate (1.36 g, 7.86 mmol) was added and stirring was continued for 2 h. Water (10 mL) was added and the mixture was extracted with ethyl acetate (40 mL). The combined organic layers were washed with brine (10 mL) and dried over sodium sulfate. Concentration and purification of the residue by chromatography (SiO$_2$, heptane:ethyl acetate=80:20 to 50:50, 1.00 g, 47%) which was obtained as a light yellow oil. MS: m/e=326.2 [M+H]$^+$.

EXAMPLE 2

5-(5-Methyl-3-phenyl-isoxazol-4-ylmethoxy)-pyrazine-2-carboxylic acid cyclopropylmethyl-amide a) 5-(5-Methyl-3-phenyl-isoxazol-4-ylmethoxy)-pyrazine-2-carboxylic acid To a solution of 5-(5-methyl-3-phenyl-isoxazol-4-yl-methoxy)-pyrazine-2-carboxylic acid methyl ester (1.00 g, 3.07 mmol) (1.0 g, 1.69 mmol) in ethanol (10 mL) was added aqueous sodium hydroxide (1 N, 6.2 mL). After heating at 60° C. for 30 min it was cooled to ambient temperature and aqueous sodium carbonate (2 M, 50 mL) added. Addition of aqueous sodium hydroxide (1 M, 50 mL) was followed by extraction with tert-butylmethylether. The aqueous phase was acidified with aqueous hydrogen chloride (25%) to pH=2 and extracted with tert-butylmethylether and ethyl acetate. The combined organic layers were dried over sodium sulfate and concentration afforded the title compound (450 mg, 86%) as a white foam. MS: m/e=310.5 [M−H]$^−$.

b) 5-(5-Methyl-3-phenyl-isoxazol-4-ylmethoxy)-pyrazine-2-carboxylic acid cyclopropylmethyl-amide To a solution of 5-(5-methyl-3-phenyl-isoxazol-4-yl-methoxy)-pyrazine-2-carboxylic acid (150 mg, 0.48 mmol) in DMF (2 mL) were added 2-(1H-benzotriazole-1-yl)-1,1,3,3-tetramethyluronium tetrafluoroborate (170 mg, 0.55 mmol), N,N-diisopropyl ethyl amine (410 μL, 2.4 mmol) and aminomethylcyclopropane (41 mg, 0.58 mmol). The resulting reaction mixture was stirred for 30 min at room temperature and diluted with water. The mixture was then extracted with ethyl acetate and the combined organic layers washed with aqueous sodium carbonate (saturated) and dried over sodium sulfate. Concentration and purification by chromatography (SiO$_2$, heptane:ethyl acetate=90:10 to 60:40, 117 mg, 67%) which was obtained as an off-white solid. MS: m/e=365.3 [M+H]$^+$.

EXAMPLE 3

5-(5-Methyl-3-phenyl-isoxazol-4-ylmethoxy)-pyrazine-2-carboxylic acid isopropylamide As described for example 2b, 5-(5-methyl-3-phenyl-isoxazol-4-ylmethoxy)-pyrazine-2-carboxylic acid (100 mg, 0.32 mmol), was converted, using isopropylamine instead of aminomethylcyclopropane, to the title compound (SiO$_2$, heptane:ethyl acetate=90:10 to 60:40, 37 mg, 33%) which was obtained as an off-white solid. MS: m/e=353.2 [M+H]$^+$.

EXAMPLE 4

5-(5-Methyl-3-phenyl-isoxazol-4-ylmethoxy)-pyrazine-2-carboxylic acid tert-butylamide As described for example 2b, 5-(5-methyl-3-phenyl-isoxazol-4-ylmethoxy)-pyrazine-2-carboxylic acid (100 mg, 0.32 mmol) was converted using tert-butylamine instead of aminomethylcyclopropane, to the title compound (SiO$_2$, heptane:ethyl acetate=90:10 to 60:40, 24 mg, 20%) which was obtained as a colorless gum. MS: m/e=367.2 [M+H]$^+$.

EXAMPLE 5

5-(5-Methyl-3-phenyl-isoxazol-4-ylmethoxy)-pyrazine-2-carboxylic acid cyclopropylamide As described for example 2b, 5-(5-methyl-3-phenyl-isoxazol-4-ylmethoxy)-pyrazine-2-carboxylic acid (100 mg, 0.32 mmol) was converted, using cyclopropylamine instead of aminomethylcyclopropane, to the title compound (SiO$_2$, heptane:ethyl acetate=90:10 to 60:40, 32 mg, 28%) which was obtained as a white solid. MS: m/e=351.3 [M+H]$^+$.

EXAMPLE 6

5-(5-Methyl-3-phenyl-isoxazol-4-ylmethoxy)-pyrazine-2-carboxylic acid (tetrahydro-pyran-4-yl)-amide As described for example 2b, 5-(5-methyl-3-phenyl-isoxazol-4-ylmethoxy)-pyrazine-2-carboxylic acid (125 mg, 0.40 mmol) was converted, using 4-aminotetrahydropyran instead of aminomethylcyclopropane to the title compound (SiO$_2$, heptane:ethyl acetate=70:30 to 40:60, 73 mg, 46%) which was obtained as a white solid. MS: m/e=395.1 [M+H]$^+$.

EXAMPLE 7

5-(5-Methyl-3-phenyl-isoxazol-4-ylmethoxy)-pyrazine-2-carboxylic acid (4,4-difluoro-cyclohexyl)-amide As described for example 2b, 5-(5-methyl-3-phenyl-isoxazol-4-ylmethoxy)-pyrazine-2-carboxylic acid (100 mg, 0.32 mmol) was converted, using 4,4-difluorocyclohexylamine instead of aminomethylcyclopropane to the title compound (SiO$_2$, heptane:ethyl acetate=90:10 to 60:40, 37 mg, 27%) which was obtained as a white solid. MS: m/e=429.2 [M+H]$^+$.

EXAMPLE 8

2-(5-Methyl-3-phenyl-isoxazol-4-ylmethoxy)-quinoxaline

To a solution of (5-methyl-3-phenyl-isoxazol-4-yl)-methanol (100 mg, 0.53 mmol) in THF (6 mL) was added 2-hydroxyquinoxaline (77 mg, 0.53 mmol) and tributyl phosphine (206 µL, 0.79 mmol) at ambient temperature under an argon atmosphere. After cooling to 0° C., N,N,N',N'-tetramethylazodicarboxamide (137 mg, 0.79 mmol) was added. The resulting orange solution was stirred for 16 h at ambient temperature followed by 2.5 h at 50° C. Then triphenylphosphine (208 mg, 0.79 mmol), 2-hydroxyquinoxaline (77 mg, 0.53 mmol) and diethyl azodicarboxylate (127 µL, 0.79 mmol) were added and the reaction mixture was stirred for 4 h at 50° C. The reaction mixture was then evaporated. Purification by chromatography (SiO$_2$, heptane:ethyl acetate=95:5 to 0:100) afforded the title compound (67 mg, 40%) as a white solid. MS: m/e=318.2 [M+H]$^+$.

EXAMPLE 9

5-[(5-Methyl-3-phenyl-isoxazol-4-ylmethyl)-amino]-pyrazine-2-carboxylic acid isopropylamide a) 5-[(5-Methyl-3-phenyl-isoxazol-4-ylmethyl)-amino]-pyrazine-2-carboxylic acid methyl ester A solution of (5-methyl-3-phenyl-4-isoxazolyl)methylamine (2.4 g, 12.7 mmol) and 5-chloro-pyrazine-2-carboxylic acid methyl ester (2.2 g, 12.7 mmol) in DMSO (15 mL) was heated with microwave irradiation to 160° C. for 30 min. After cooling to room temperature the reaction mixture was extracted (ethyl acetate/water). The organic phase was dried over sodium sulfate, concentrated and chromatographed (SiO$_2$, heptane:ethyl acetate=100:0 to 20:80). The oily product obtained was triturated with diisopropylether and ethyl acetate to afford the title compound (3.5 g, 84% as an off-white solid. MS: m/e=325.4 [M+H]$^+$.

b) 5-[(5-Methyl-3-phenyl-isoxazol-4-ylmethyl)-amino]-pyrazine-2-carboxylic acid isopropylamide To a solution of isopropylamine (0.69 mL, 8 mmol) in dioxane (5 mL) was added dropwise trimethylaluminum solution (2M solution in hexane, 4 mL, 8 mmol). After stirring for 1 h at room temperature a suspension of 5-[(5-methyl-3-phenyl-isoxazol-4-ylmethyl)-amino]-pyrazine-2-carboxylic acid methyl ester (650 mg, 2 mmol) in dioxane (5 mL) was added. The reaction mixture was stirred at 90° C. for 90 min, cooled to room temperature and poured into water. Extraction (ethyl acetate/saturated aqueous Seignette salt solution) followed by drying of the organic phase over sodium sulfate and evaporation afforded an oil. Purification by chromatography (SiO$_2$, heptane:ethyl acetate=100:0 to 20:80) afforded the title compound (600 mg, 85%) as a white solid MS: m/e=352.3 [M+H]$^+$.

EXAMPLE 10

5-[(5-Methyl-3-phenyl-isoxazol-4-ylmethyl)-amino]-pyrazine-2-carboxylic acid cyclopropylamide As described for example 9b, 5-[(5-methyl-3-phenyl-isoxazol-4-ylmethyl)-amino]-pyrazine-2-carboxylic acid methyl ester (650 mg, 2 mmol) was converted, using cyclopropylamine instead of isopropylamine, to the title compound (600 mg, 86%) which was obtained as a white solid. MS: m/e=394.3 [M+H]$^+$.

EXAMPLE 11

5-[(5-Methyl-3-phenyl-isoxazol-4-ylmethyl)-amino]-pyrazine-2-carboxylic acid (tetrahydro-pyran-4-yl)-amide As described for example 9b, 5-[(5-methyl-3-phenyl-isoxazol-4-ylmethyl)-amino]-pyrazine-2-carboxylic acid methyl ester (650 mg, 2 mmol) was converted, using 4-aminotetrahydropyran instead of isopropylamine, to the title compound (640 mg, 81%) which was obtained as a white solid. MS: m/e=350.4 [M+H]$^+$.

The invention claimed is:

1. A compound of formula I

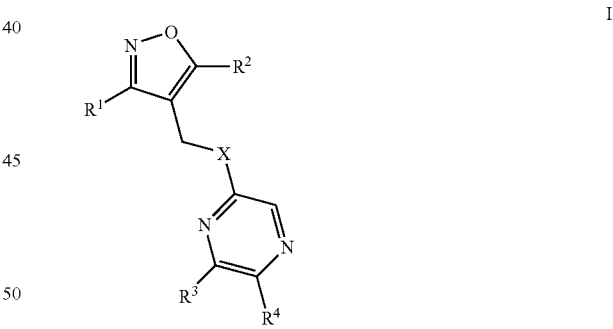

wherein
X is O or NH;
R$^1$ is phenyl, optionally substituted with one, two or three halo,
R$^2$ is H, C$_{1-4}$ alkyl or C$_{1-4}$ haloalkyl;
R$^3$ and R$^4$ each are independently
H,
C$_{1-7}$ alkyl, optionally substituted with one or more halo, cyano, or hydroxy,
C$_{1-7}$ alkoxy, optionally substituted with one or more halo,
CN,
halo,
NO$_2$, —C(O)—R$^a$, wherein R$^a$ is hydroxy, C$_{1-7}$ alkoxy, C$_{1-7}$ alkyl, phenoxy or phenyl, —C(O)—NR$^b$R$^c$, wherein R$^b$ and R$^c$ are each independently

H,

C$_{1-7}$ alkyl, optionally substituted with one or more halo, hydroxy, or cyano, —(CH$_2$)$_z$—C$_{3-7}$ cycloalkyl, optionally substituted by one or more B, and z is 0, 1, 2, 3 or 4, —(CH$_2$)$_y$-heterocyclyl, wherein y is 0, 1, 2, 3 or 4, and wherein heterocyclyl is optionally substituted by one or more A R$^b$ and R$^c$ together with the nitrogen to which they are bound form a heterocyclyl moiety, optionally substituted with one or more A, or or R$^3$ and R$^4$ together form an annelated benzo ring, the benzo ring is optionally substituted by one or more E;

A is hydroxy, oxo, C$_{1-7}$ alkyl, C$_{1-7}$ alkoxy, C$_{1-7}$ haloalkyl, C$_{1-7}$ hydroxyalkyl, halo, or CN;

B is halo, hydroxy, CN, C$_{1-4}$ alkyl, or C$_{1-4}$ haloalkyl;

E is halo, CN, NO$_2$, hydroxy, C$_{1-7}$ alkyl, C$_{1-7}$ alkoxy, C$_{1-7}$ haloalkyl, C$_{1-7}$ hydroxyalkyl, C$_{1-7}$ cyanoalkyl, C$_{1-7}$ haloalkoxy, or C$_{3-7}$ cycloalkyl, or a pharmaceutically acceptable salt thereof.

2. The compound of claim 1, wherein R$^2$ is hydrogen, methyl, or trifluoromethyl.

3. The compound of claim 2, wherein R$^2$ is hydrogen or methyl.

4. The compound of claim 3, wherein R$^2$ is methyl.

5. The compound of claim 1, wherein R$^1$ is phenyl optionally substituted with one, two, or three halo.

6. The compound of claim 5, wherein halo is chloro or fluoro.

7. The compound of claim 5, wherein the phenyl is substituted with one or two chloro or fluoro.

8. The compound of claim 1 wherein

R$^3$ is H, or

R$^3$ and R$^4$ together form an annelated benzo ring, the benzo ring is optionally substituted by one or more halo, CN, NO$_2$, hydroxy, C$_{1-7}$ alkyl, C$_{1-7}$ alkoxy, C$_{1-7}$ haloalkyl, or C$_{1-7}$ hydroxyalkyl.

9. The compound of claim 1, wherein

R$^4$ is H,

—C(O)—R$^a$, wherein R$^a$ is hydroxy, C$_{1-7}$ alkoxy, C$_{1-7}$ alkyl, phenoxy or phenyl, —C(O)—NR$^b$R$^c$, wherein R$^b$ and R$^c$ are each independently

H,

C$_{1-7}$ alkyl, optionally substituted with one or more halo, hydroxy, or cyano, —(CH$_2$)$_z$—C$_{3-7}$ cycloalkyl, optionally substituted by one or more B, and z is 0, 1, 2, 3 or 4, —(CH$_2$)$_y$-heterocyclyl, wherein y is 0, 1, 2, 3 or 4, and wherein heterocyclyl is optionally substituted by one or more A or R$^3$ and R$^4$ together form an annelated benzo ring, the benzo ring is optionally substituted by one or more E, A is hydroxy, oxo, C$_{1-7}$ alkyl, C$_{1-7}$ alkoxy, C$_{1-7}$ haloalkyl, C$_{1-7}$ hydroxyalkyl, halo, or CN;

B is halo, hydroxy, CN, C$_{1-4}$ alkyl, or C$_{1-4}$ haloalkyl;

E is halo, CN, NO$_2$, hydroxy, C$_{1-7}$ alkyl, C$_{1-7}$ alkoxy, C$_{1-7}$ haloalkyl, C$_{1-7}$ hydroxyalkyl, C$_{1-7}$ cyanoalkyl, C$_{1-7}$ haloalkoxy, or C$_{3-7}$ cycloalkyl.

10. The compound of claim 1, selected from the group consisting of 5-(5-methyl-3-phenyl-isoxazol-4-ylmethoxy)-pyrazine-2-carboxylic acid methyl ester, 5-(5-methyl-3-phenyl-isoxazol-4-ylmethoxy)-pyrazine-2-carboxylic acid cyclopropylmethyl-amide, 5-(5-methyl-3-phenyl-isoxazol-4-ylmethoxy)-pyrazine-2-carboxylic acid isopropylamide, 5-(5-methyl-3-phenyl-isoxazol-4-ylmethoxy)-pyrazine-2-carboxylic acid tert-butylamide, 5-(5-methyl-3-phenyl-isoxazol-4-ylmethoxy)-pyrazine-2-carboxylic acid cyclopropylamide, 5-(5-methyl-3-phenyl-isoxazol-4-ylmethoxy)-pyrazine-2-carboxylic acid (tetrahydro-pyran-4-yl)-amide, 5-(5-methyl-3-phenyl-isoxazol-4-ylmethoxy)-pyrazine-2-carboxylic acid (4,4-difluoro-cyclohexyl)-amide, 2-(5-methyl-3-phenyl-isoxazol-4-ylmethoxy)-quinoxaline, 5-[(5-methyl-3-phenyl-isoxazol-4-ylmethyl)-amino]-pyrazine-2-carboxylic acid isopropylamide, 5-[(5-methyl-3-phenyl-isoxazol-4-ylmethyl)-amino]-pyrazine-2-carboxylic acid cyclopropylamide, and 5-[(5-methyl-3-phenyl-isoxazol-4-ylmethyl)-amino]-pyrazine-2-carboxylic acid (tetrahydro-pyran-4-yl)-amide.

11. A pharmaceutical composition comprising a compound of formula I

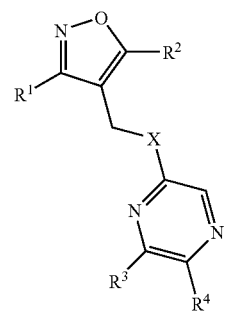

I wherein

X is O or NH;

R$^1$ is phenyl, optionally substituted with one, two or three halo,

R$^2$ is H, C$_{1-4}$ alkyl or C$_{1-4}$ haloalkyl;

R$^3$ and R$^4$ each are independently

H,

C$_{1-7}$ alkyl, optionally substituted with one or more halo, cyano, or hydroxy, C$_{1-7}$ alkoxy, optionally substituted with one or more halo,

CN, halo,

NO$_2$,

—C(O)—R$^a$, wherein R$^a$ is hydroxy, C$_{1-7}$ alkoxy, C$_{1-7}$ alkyl, phenoxy or phenyl, —C(O)—NR$^b$R$^c$, wherein R$^b$ and R$^c$ are each independently

H,

C$_{1-7}$ alkyl, optionally substituted with one or more halo, hydroxy, or cyano, —(CH$_2$)$_z$—C$_{3-7}$ cycloalkyl, optionally substituted by one or more B, and z is 0, 1, 2, 3 or 4, —$(CH_2)_y$-heterocyclyl, wherein y is 0, 1, 2, 3 or 4, and wherein heterocyclyl is optionally substituted by one or more A $R^b$ and $R^c$ together with the nitrogen to which they are bound form a heterocyclyl moiety, optionally substituted with one or more A, or or $R^3$ and $R^4$ together form an annelated benzo ring, the benzo ring is optionally substituted by one or more E;

A is hydroxy, oxo, $C_{1-7}$ alkyl, $C_{1-7}$ alkoxy, $C_{1-7}$ haloalkyl, $C_{1-7}$ hydroxyalkyl, halo, or CN;

B is halo, hydroxy, CN, $C_{1-4}$ alkyl, or $C_{1-4}$ haloalkyl;

E is halo, CN, $NO_2$, hydroxy, $C_{1-7}$ alkyl, $C_{1-7}$ alkoxy, $C_{1-7}$ haloalkyl, $C_{1-7}$ hydroxyalkyl, $C_{1-7}$ cyanoalkyl, $C_{1-7}$ haloalkoxy, or $C_{3-7}$ cycloalkyl, or a pharmaceutically acceptable salt thereof and a pharmaceutically acceptable carrier.

\* \* \* \* \*